US00PP21631P3

(12) United States Plant Patent
Chang

(10) Patent No.: US PP21,631 P3
(45) Date of Patent: Jan. 18, 2011

(54) MANGO TREE 'FP2'

(50) Latin Name: *Mangifera indica*
Varietal Denomination: FP2

(76) Inventor: Min-Hsien Chang, 1, 2 Lin, Ne-Won Village, Fan-Ru Shiang, Chia-Yi Hsien (TW) 60243

( * ) Notice: Subject to any disclaimer, the term of this patent is extended or adjusted under 35 U.S.C. 154(b) by 32 days.

(21) Appl. No.: 12/289,007

(22) Filed: Oct. 17, 2008

(65) Prior Publication Data

US 2010/0100993 P1 Apr. 22, 2010

(51) Int. Cl.
*A01H 5/00* (2006.01)

(52) U.S. Cl. ..... Plt./159

(58) Field of Classification Search ..... Plt./159
See application file for complete search history.

(56) References Cited

U.S. PATENT DOCUMENTS

PP9,005 P 12/1994 Chang

*Primary Examiner*—June Hwu
(74) *Attorney, Agent, or Firm*—Jacobson Holman PLLC

(57) ABSTRACT

The invention is directed to a new mango tree variety 'FP2' which is the mutation of the parent cultivar 'FP1'. The mango tree produces medium a little red fruit on a yellow ground color, and matured in August. The fruit seems to be resistant to Anthracnose and good storage capacity. The flesh of the fruit is orange yellow, high juice content, low fiber content, low acidity, good taste with high sugar content. The core is small.

4 Drawing Sheets

Latin name of the genus and species of the plant claimed: The Latin name of the genus of mango is *Mangifera.* The Latin name of the species of mango is *Mangifera indica.*

BACKGROUND OF THE INVENTION

1. Field of the Invention

This invention relates to a new variety of tropical mango.

2. Description of the Related Art

This inventor has a U.S. Plant Pat. No. 9,005 entitled Mango Tree FP1 (hereafter to be called 'FP1'). He has repeatedly asexually reproduced by planting of the buds of 'FP1' in the ground at the Chia-Yi of Taiwan to form an orchard. Such asexual reproduction uniformly produces a fruit of the character described in the specification of the U.S. Plant Pat. No. 9,005. In 2000, he discovered in the orchard that the fruit of a mango tree only has 'FP1' mango's partial characteristic, which are not similar with the other 'FP1' fruit. The mango of the discovered variety is referred to as the 'FP2' mango. The new variety 'FP2' is a true mutation of the parent cultivar 'FP1'. The claimed plant 'FP2'was found from a sport in a cultivated area in Applicant's orchard. The age of the observed plant is 8 years old. The new variety of mango tree has been repeatedly asexually reproduced in this applicant's orchard at the Chia-Yi Hsien of Taiwan by placing budwood of 'FP2', on mango seedlings in April 2006. Such asexual reproductions consistently and uniformly produce fruits of the characteristics described in this specification.

SUMMARY OF THE INVENTION

The invention is directed to a new mango tree variety 'FP2' which is the mutation of the parent cultivar 'FP1'. The mango tree produces medium a little red fruit on a yellow ground color, and matured in August. The fruit seems to be resistant to Anthracnose and good storage capacity. The flesh of the fruit is orange yellow, high juice content, low fiber content, low acidity, good taste with high sugar content. The core is small, and white color near 158C.

BRIEF DESCRIPTION OF THE DRAWINGS

A new variety of tropical mango is shown in the drawings FIGS. 1 to 8.

Figure 1:
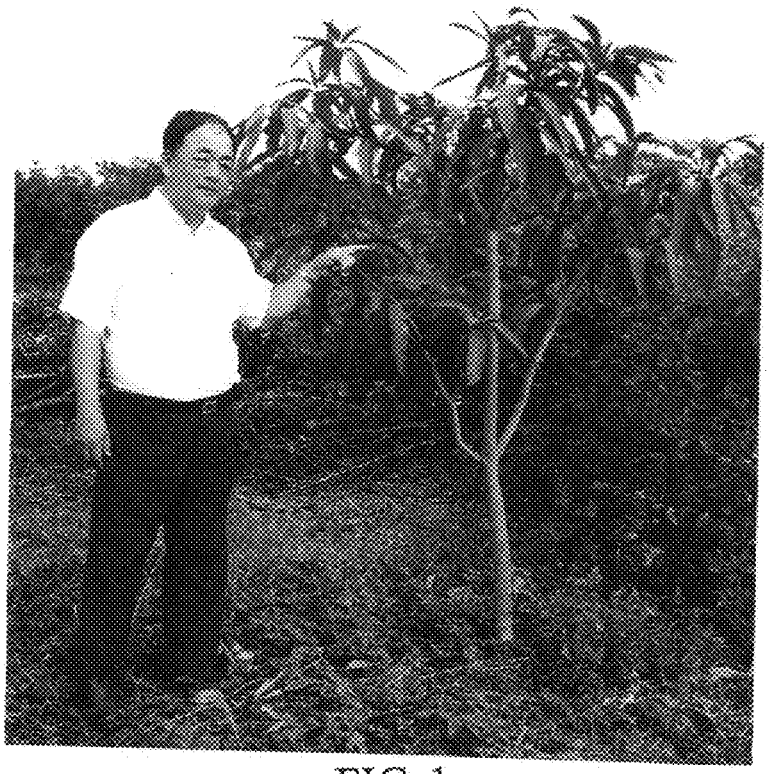
FIG. 1 is a photograph of the original tree of 'FP2'.
Figure 2:
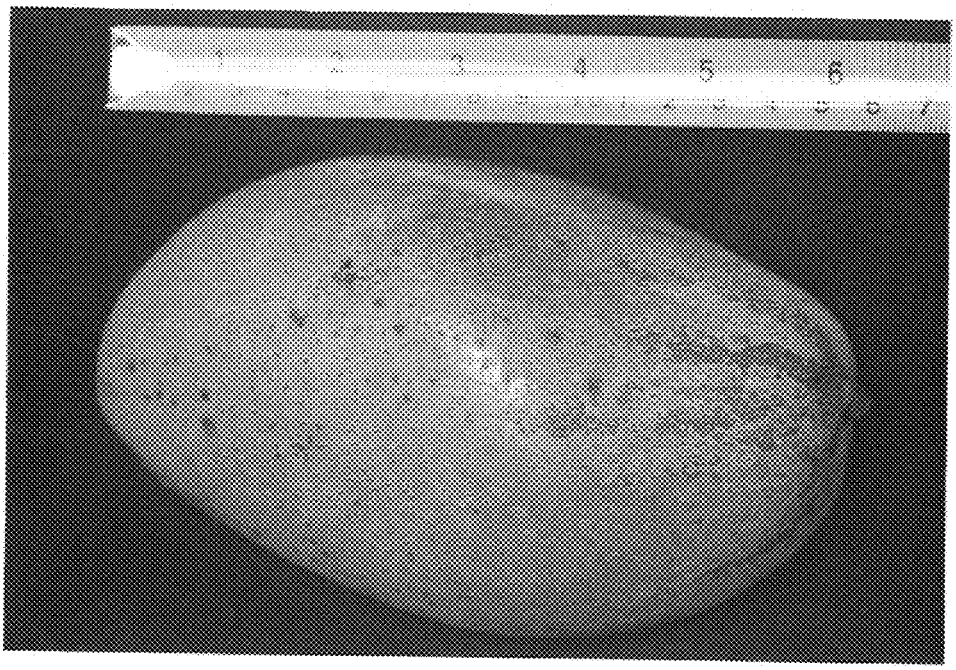
Figure 3:
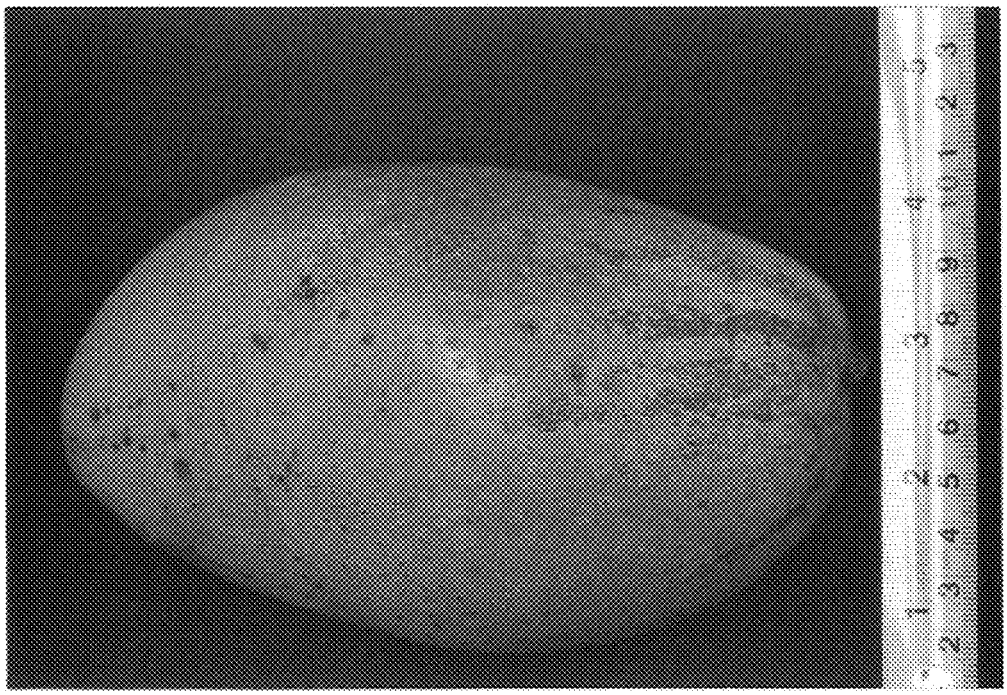

Each of FIGS. 2-3 is a photograph of the fruit of 'FP2'.

Figure 4:
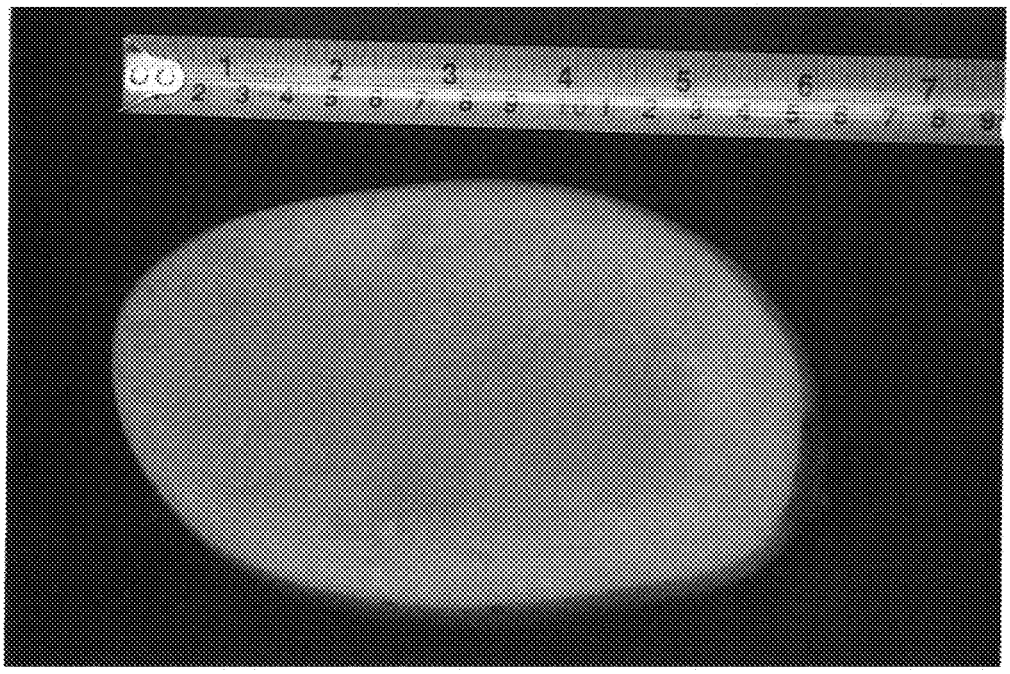

FIGS. 4 is a photograph of a cross-section of 'FP2' fruit.

Figure 5:
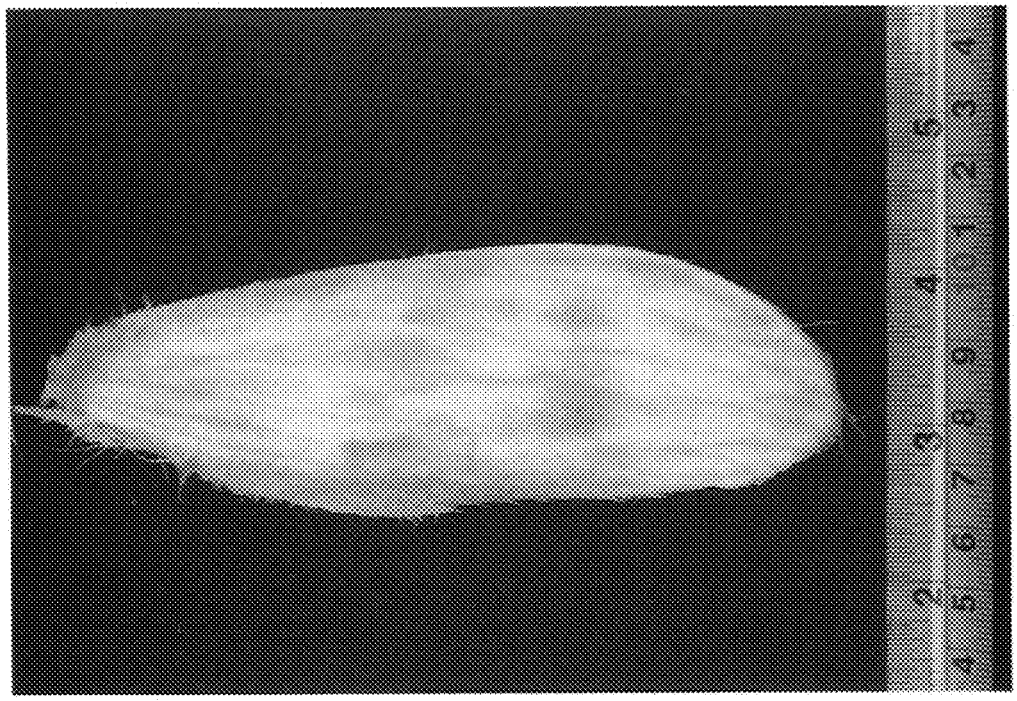
Figure 6:
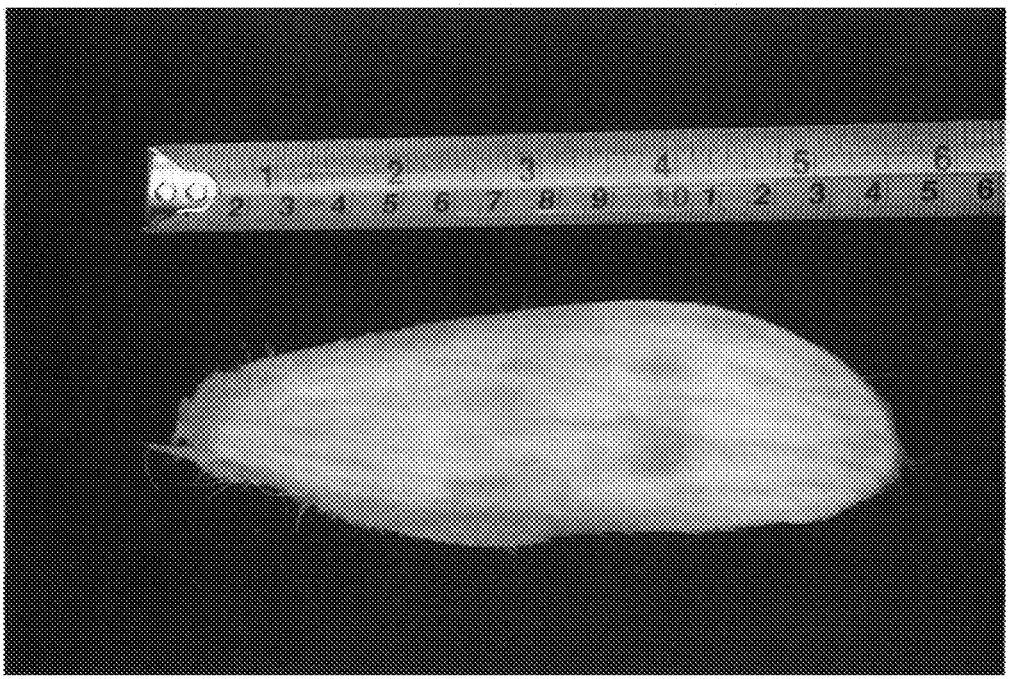

Each of FIGS. 5-6 is a photograph of a core of 'FP2'.

Figure 7:
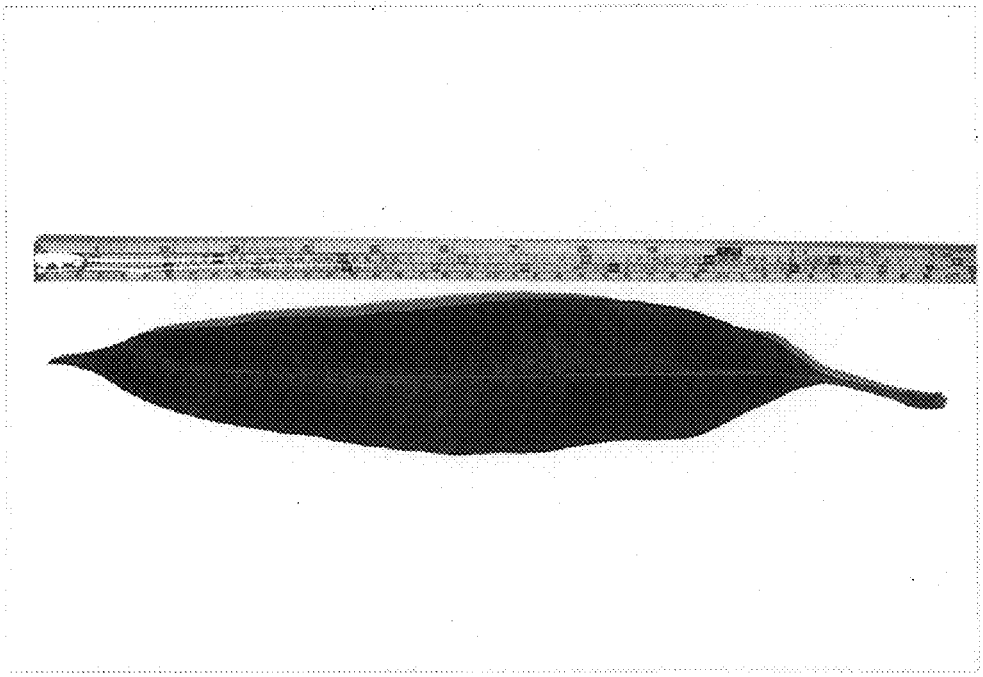
Figure 8:
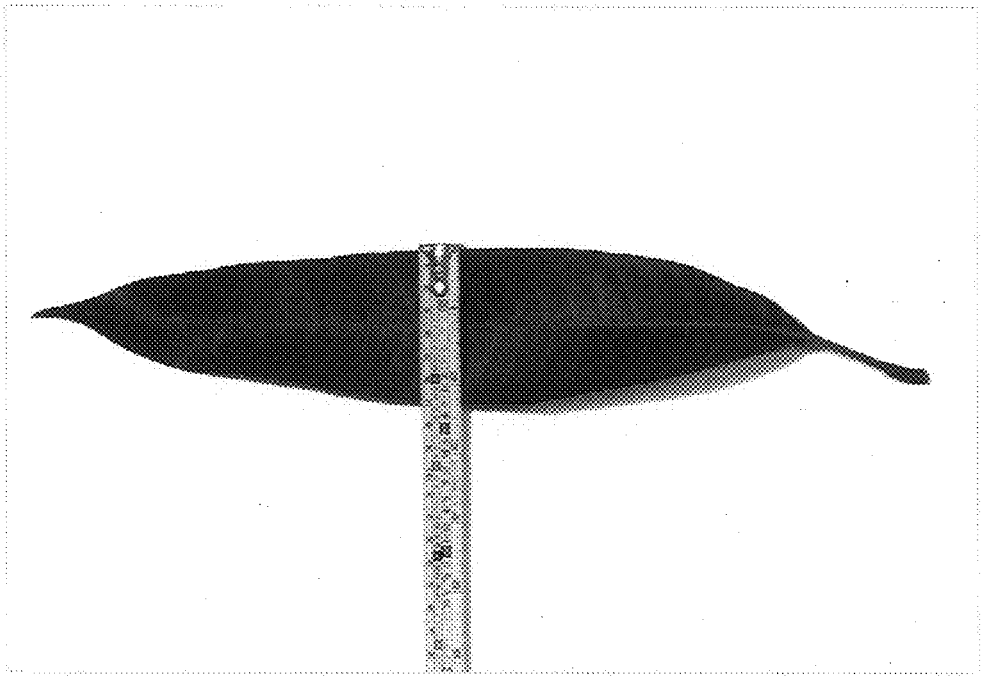

Each of FIGS. 7-8 is a photograph of a leaf of 'FP2'.

DETAILED DESCRIPTION OF THE INVENTION

The following is a description of the characteristics of the mango tree variety of this invention.

Tree:

*Tree vigor.*—Medium. The terminal growth during the winter is 15 cm, and during the summer is 30 cm.

*Tree size.*—Medium about 8 years old.

*Tree type.*—Long oval.

*Height.*—3 m.

*Girth.*—40 cm. The measurement tree trunk was taken at the height of 60 cm from the earth ground.

*Maturity.*—The fruit of the tree ripens in August.

*Pollination.*—Open pollinated.

*Location.*—Chia-Yi, Taiwan.

*Pruning.*—Twice a year. The first time is in spring, any time at its bearing. The bent flower stalk without fruits and the slim twigs should be cut out for easy management. The second time is in summer, any time after the harvest. The upward branches should be cut out for high productivity in the next season.

*Bark.*—Smooth.

*Petiolate.*—Tough, resistant to wind damage.

*Bloom.*—Early, on December, full blooming on February. The location at time of culture of the blooming season of the instant tree is in winter at the Chia-Yi Hsien located in the middle of Taiwan.

Leaf:

*Length.*—34.5 cm.

*Width.*—7.0 cm.

*Thickness.*—0.5 cm.

*Color.*—Both the upper and the lower leaf surface is green color near 136A.

*Leaf type.*—Large, oval-lanceolate, The tip of a branch is personate verticillate phyllotaxy.

*Both upper and lower leaves' surface.*—Glabrous and smooth.

*Petiolate.*—5.5 cm in length. The petiole's color is green near 136A. The petiole's surface texture is glabrous and smooth.

The leaf's margin is entire, is not serrated. The apex shape of leaf is acute tip. The base shape of the leaf is lanceolate.

The leaves are simple, exstipulate, alternately arranged, 34.5 cm in length. The petiole is 5.5 cm in length, always swollen at the base. It is grooved on the upper side. As the leaves are arranged very closely at the tips they appear to be whorled. The shape of leaves is lanceolate. The apex ranges from acuminate to nearly rounded. The margin is usually entire, sometimes slightly undulated and wavy, rarely twisted or folded. The length and breadth varies from 12 to 45 cm and 2 to 12 cm, respectively, depending on variety and growth. The secondary veins are quite prominent, and in some of the varieties range from eighteen to thirty pairs. The upper surface is shining and dark green while the lower is glabrous light green. The leaves appear in flushes. They are flaccid and pendulous when young. The color of young leaves generally varies form variety to variety, generally being tan-red, pink, yellow-brown in color. As the leaf grows, its color changes from tan-red to green, passing through many different shades and becomes dark green at maturity.

The leaves have fibres and crackle when crushed. They have strongly smell of turpentine (some cultivars do not smell). The leaves contain a good amount of mangiferin (xanthone). In India, it was obtained as "Indian Yellow" from the cow's urine because cows were fed exclusively with mango leaves and ultimately excessive feeding on leaves lead to the death of the animal.

Panicle:

*Inflorescence.*—Conic, axil and terminal, the inflorescence length being about 15-40 cm, normally having ramify 2 or 3 times and the last ramification has 3 flowers as an umbrella. Every inflorescence has 500-3,000 flowers. The inflorescence length is 15-40 cm. The diameter of the flower is 0.25-0.3 cm. The length of the flower is 0.2 cm.

*Calyx.*—5 pieces. The calyx's average size is 0.2 cm, yellow color near 13A.

*Petal.*—5 pieces. The petal's average size is 0.2 cm, yellow color near 13A.

*Stamen.*—5 pieces, but normally only 2 or 3 stamen in full growth could disseminate pollen. And, the shape of a grain of the pollen is oval. The color of the pollen is yellow near 13A.

*Flower.*—Has the staminate flower and the gynandrous flower. The average of the gynandrous flower is 3-60%. The number of pistil per flower is 5 pieces.

Fruit:

*Weight.*—995.6 g.

*Size.*—Axial diameter 157 mm. Transverse diameter 87 mm.

*Skin color.*—A little red (near 169B) on a yellow (near 163C) ground.

*Flesh.*—Orange yellow near 163B, juicy, low fiber content, good taste.

*Aroma.*—Comparable to the local mango variety.

*Sweetness.*—High sugar content (Brix 16).

*Acid.*—Low acidity (0.12%).

*Thickness of Skin.*—0.9-1.1 mm.

*Fruit count per panicle.*—2-3 pieces.

*Storage.*—The fruit will drop in a protective bag about 3 days after maturity. The fruit can be held without any handling requirements for about 20 days.

*Susceptibility to bruising.*—Not easy.

Core:

*Weight.*—43.55 g.

*Size.*—Axial diameter 143 mm. Transverse diameter 42 mm.

*Fiber.*—Only a latter around the core. The Core has along its latter peak a beard of short fibers.

The stone's average size is small, 143 mm in axial diameter and 42 mm in transverse diameter. The surface texture is striated. The shape is flat and elongated.

The mature fruit's shape is elliptic. Its ventral shoulder shape is round. Its dorsal shoulder shape is round. The surface texture is glabrous and smooth. The fruit lenticel's density is five holes per 1 $cm^2$. Each hole's average size is 0.05 cm. The average depth of the fruit stalk cavity is 0.05 cm. The ripe fruit adherence of the skin to the flesh is easy to separate. The ripe fruit flesh's firmness is hard. The ripe fruit flesh's juiciness is high juice content. The ripe fruit flesh's texture is low fiber content. When fully ripe, some fruits have a "turpentine" fresh odor and flavor.

The average size of the seed is small. The length of the seed is 8 cm. The width of the seed is 2 cm. The thickness of the seed is 0.4 cm. The shape of the seed is flat and elongated. The color of the seed is white. The type of seed embryony is monoembryonic.

The tree and fruit seems to be resistant to Anthracnose, diseases and pest. The types of diseases to which the tree and fruit of FP2 are resistant include Anthracnose, Powdery mildew. The types of major pests of mango to which the tree and fruit of FP2 are resistant are *Idioscopus* species, such as *Idioscopus clypealis* Lethierry, *Idioscopus niveosparsus* Lethierry, *Idioscopus nitidulus* Walker and *Scirtothrips dorsalis* Hood, *Thrips hawaiiensis* (Morgan), *Chlumetia transversa* (Walker), fruitfly.

The plant perfect temperature ranged from 20° C. to 25° C. The hardiness zone is not observed. Remarks: All color values expressed herein are those of The R.H.S. Colour Chart.

A list comparing FP2, FP1 and F1 is showed in Table 1 below:

TABLE 1

LIST OF COMPARISON BETWEEM FP2, FP1, AND F1

| | FP2 | FP1 | F1 |
|---|---|---|---|
| Leaf | | | |
| Length | 34.5 cm | 30.5 cm | 29 cm |
| Width | 7.0 cm | 6.5 cm | 8.5 cm |

TABLE 1-continued

| LIST OF COMPARISON BETWEEM FP2, FP1, AND F1 | | | |
|---|---|---|---|
| | FP2 | FP1 | F1 |
| Thickness | 0.5 cm | 0.5 cm | 0.5 cm |
| Color | Green near 136A | Green near 143B | Dark green near 135B |
| Petiole | 5.5 cm in length | 6.5 cm | 5 cm |
| Fruit | | | |
| Weight | 995.6 g | 553.8 g | 412 g |
| Shape | Long oval but its apex much more round | Long oval but much more round | Long oval but much more flat |
| Flesh | Very little fibers; easy to separate from its skin | A little fibers | No fibers |
| Skin color | A little red (near 169B) on a yellow (near 163C) ground | Red near 45B or 70B on a green (149B) ground, but will change as red (45A) on a yellow (14B) ground | Green near 143B but will change as yellow near 9A when matured |
| Thickness of skin | 0.9-1.1 mm | 0.8-1.0 mm | 0.7-0.9 mm |
| Core | | | |
| Weight | 43.55 g | 43.8 g | 35.6 g |
| Size | Axial diameter 143 mm, transverse diameter 42 mm. | Axial diameter 142.6 mm; transverse diameter 40.3 mm. Core is easy to separate from the flesh like Irwin. | Axial diameter 151 mm; transverse diameter 37.6 mm; |
| Seed | | | |
| Weight | 15 g | 21.3 g | 17.3 g |
| Size | Axial diameter 80 mm; transverse diameter 20 mm | Axial diameter 74.4 mm; transverse diameter 30.5 mm | Axial diameter 76 mm; transverse diameter 28.2 mm |
| Tree | | | |
| Size | Medium about 8 years old | Medium about 21 years old | High |
| Branch | Rare | Rare | Dense |
| Bark | Smooth | Smooth | Rough |
| Vein | Same with FP1 | Same color with the leaf but a little slice red (45B) in the early leafing about 7 days of each time | Same color with the leaf |

The invention claimed is:

1. A new and distinct mango tree variety ‘FP2’ as shown and described, to be a true mutation of the parent cultivar ‘FP1’.

* * * * *